(12) United States Patent
Leuthardt

(10) Patent No.: US 11,045,134 B2
(45) Date of Patent: Jun. 29, 2021

(54) DEPRESSION BRAIN COMPUTER INTERFACE FOR THE QUANTITATIVE ASSESSMENT OF MOOD STATE AND FOR BIOFEEDBACK FOR MOOD ALTERATION

(71) Applicant: Washington University, St. Louis, MO (US)

(72) Inventor: Eric Leuthardt, St. Louis, MO (US)

(73) Assignee: Washington University, St. Louis, MO (US)

( * ) Notice: Subject to any disclaimer, the term of this patent is extended or adjusted under 35 U.S.C. 154(b) by 687 days.

(21) Appl. No.: 15/410,411

(22) Filed: Jan. 19, 2017

(65) Prior Publication Data
US 2017/0202475 A1 Jul. 20, 2017

Related U.S. Application Data

(60) Provisional application No. 62/280,368, filed on Jan. 19, 2016.

(51) Int. Cl.
*A61B 5/16* (2006.01)
*A61B 5/316* (2021.01)
(Continued)

(52) U.S. Cl.
CPC .............. *A61B 5/316* (2021.01); *A61B 5/165* (2013.01); *A61B 5/369* (2021.01); *A61B 5/7405* (2013.01); *A61B 5/24* (2021.01); *A61B 5/4848* (2013.01)

(58) Field of Classification Search
CPC . A61B 5/0478; A61B 5/04012; A61B 5/6803; A61B 5/165
See application file for complete search history.

(56) References Cited

U.S. PATENT DOCUMENTS 7,373,198 B2   5/2008   Stéphane et al.
7,570,991 B2   8/2009   Milgramm
(Continued)

FOREIGN PATENT DOCUMENTS

WO   2014172775 A1   10/2014
WO   2015164477 A1   10/2015

OTHER PUBLICATIONS

Fingelkurts et al; Impaired Functional Connectivity at EEG Alpha and Theta Frequency Bands in Major Depression; Feb. 13, 2007; Human Brain Mapping, vol. 28 Issue 3, p. 247-261. (Year: 2007).*

(Continued)

*Primary Examiner* — Devin B Henson
*Assistant Examiner* — H. Q. Nguyen
(74) *Attorney, Agent, or Firm* — Armstrong Teasdale LLP

(57) ABSTRACT

A brain computer interface (BCI) system includes an electroencephalogram (EEG) headset and a computing device communicatively coupled to the EEG headset. The computing device includes a memory, a processor and a display device. The memory stores instructions that, when executed by the processor, cause the processor to monitor, using the EEG headset, current extrinsic network activity and current intrinsic network activity of a patient, generate a current depression index based on the relationship between the current extrinsic network activity and the current intrinsic network activity, and display, on the display device, a representation of the relationship between the current depression index and a baseline depression index previously generated for the patient.

15 Claims, 9 Drawing Sheets
(8 of 9 Drawing Sheet(s) Filed in Color)

(51) Int. Cl.
A61B 5/00 (2006.01)
A61B 5/369 (2021.01)
A61B 5/24 (2021.01)

(56) References Cited

U.S. PATENT DOCUMENTS

| | | | |
|---|---|---|---|
| 7,574,254 | B2 | 8/2009 | Milgramm |
| 7,594,122 | B2 | 9/2009 | Milgramm |
| 7,603,168 | B2 | 10/2009 | Stéphane et al. |
| 7,676,263 | B2 | 3/2010 | Harris et al. |
| 8,244,341 | B2 | 8/2012 | Hinrikus et al. |
| 8,380,314 | B2 | 2/2013 | Panken et al. |
| 8,761,869 | B2 | 6/2014 | Leuthardt |
| 8,798,735 | B1 | 8/2014 | Stéphane B et al. |
| 8,838,247 | B2 * | 9/2014 | Hagedorn ............ A61B 5/0482 607/45 |
| 2010/0069775 | A1 | 3/2010 | Milgramm |
| 2010/0125219 | A1 | 5/2010 | Harris et al. |
| 2010/0268057 | A1 | 10/2010 | Firminger et al. |
| 2010/0268108 | A1 | 10/2010 | Firminger et al. |
| 2011/0166430 | A1 | 7/2011 | Harris et al. |
| 2012/0245443 | A1 * | 9/2012 | Atsumori ............... A61B 5/165 600/328 |
| 2012/0289789 | A1 * | 11/2012 | Jain ...................... A61B 5/0022 600/301 |
| 2013/0177883 | A1 * | 7/2013 | Barnehama ............... G09B 5/00 434/236 |
| 2013/0267866 | A1 | 10/2013 | Nakashima et al. |
| 2014/0081090 | A1 * | 3/2014 | Picard ................. G06F 19/3418 600/301 |
| 2014/0107439 | A1 * | 4/2014 | Atsumori ........... A61B 5/14551 600/322 |
| 2015/0157862 | A1 * | 6/2015 | Greenberg ........... H05K 3/4061 607/60 |
| 2015/0265201 | A1 | 9/2015 | Arbas |
| 2015/0332020 | A1 * | 11/2015 | Lo ........................ A61K 31/567 702/19 |

OTHER PUBLICATIONS

Adolphs R (2009) The social brain: neural basis of social knowledge. Annu Rev Psychol 60:693-716.
Anderson JS (2008) Origin of synchronized low-frequency blood oxygen level-dependent fluctuations in the primary visual cortex. AJNR Am J Neuroradiol 29:1722-1729.
Bastiaansen MC, Oostenveld R, Jensen O, Hagoort P (2008) I see what you mean: theta power increases are involved in the retrieval of lexical semantic information. Brain Lang 106:15-28.
Buckner RL, Andrews-Hanna JR, Schacter DL (2008) The brain's default network: anatomy, function, and relevance to disease. Ann N Y Acad Sci 1124:1-38.
Buzsaki G (2002) Theta oscillations in the hippocampus. Neuron 33:325-340.
Canolty RT, Knight RT (2010) The functional role of cross-frequency coupling. Trends Cogn Sci 14:506-515.
Chang C, Glover GH (2010) Time-frequency dynamics of resting-state brain connectivity measured with fMRI. Neuroimage 50:81-98.
Corbetta M, Shulman GL (2002) Control of goal-directed and stimulus-driven attention in the brain. Nat Rev Neurosci 3:201-215.
Doucet G, Naveau M, Petit L, Delcroix N, Zago L, Crivello F, Jobard G, Tzourio-Mazoyer N, Mazoyer B, Mellet E, Joliot M (2011) Brain activity at rest: a multiscale hierarchical functional organization. J Neurophysiol 105:2753-2763.
Fedorenko E, Duncan J, Kanwisher N (2013) Broad domain generality in focal regions of frontal and parietal cortex. Proceedings of the National Academy of Sciences of the United States of America 110:16616-16621.
Fell J, Ludowig E, Staresina BP, Wagner T, Kranz T, Elger CE, Axmacher N (2011) Medial temporal theta/alpha power enhancement precedes successful memory encoding: evidence based on intracranial EEG. J Neurosci 31:5392-5397.
Foster BL, Parvizi J (2012) Resting oscillations and cross-frequency coupling in the human posteromedial cortex. Neuroimage 60:384-391.
Fox MD, Snyder AZ, Vincent JL, Corbetta M, Van Essen DC, Raichle ME (2005) The human brain is intrinsically organized into dynamic, anticorrelated functional networks. Proc Natl Acad Sci U S A 102:9673-9678.
Gholipour A, Kehtarnavaz N, Gopinath K, Briggs R, Panahi I (2008) Average field map image template for Echo-Planar image analysis. Conference proceedings : Annual International Conference of the IEEE Engineering in Medicine and Biology Society IEEE Engineering in Medicine and Biology Society Conference 2008:94-97.
Glasser MF, Sotiropoulos SN, Wilson JA, Coalson TS, Fischl B, Andersson JL, Xu J, Jbabdi S, Webster M, Polimeni JR, Van Essen DC, Jenkinson M (2013) The minimal preprocessing pipelines for the Human Connectome Project. Neuroimage 80:105-124.
Goense JB, Logothetis NK (2008) Neurophysiology of the BOLD fMRI signal in awake monkeys. Curr Biol 18:631-640.
Golland Y, Bentin S, Gelbard H, Benjamini Y, Heller R, Nir Y, Hasson U, Malach R (2007) Extrinsic and intrinsic systems in the posterior cortex of the human brain revealed during natural sensory stimulation. Cereb Cortex 17:766-777.
Griffanti L, Salimi-Khorshidi G, Beckmann CF, Auerbach EJ, Douaud G, Sexton CE, Zsoldos E, Ebmeier KP, Filippini N, Mackay CE, Moeller S, Xu J, Yacoub E, Baselli G, Ugurbil K, Miller KL, Smith SM (2014) ICA-based artefact removal and accelerated fMRI acquisition for improved resting state network imaging. Neuroimage 95:232-247.
Hacker CD, Laumann TO, Szrama NP, Baldassarre A, Snyder AZ, Leuthardt EC, Corbetta M (2013) Resting state network estimation in individual subjects. Neuroimage 82:616-633.
Hathout GM, Gopi RK, Bandettini P, Gambhir SS (1999) The lag of cerebral hemodynamics with rapidly alternating periodic stimulation: modeling for functional MRI. Magn Reson Imaging 17:9-20.
He BJ, Snyder AZ, Zempel JM, Smyth MD, Raichle ME (2008) Electrophysiological correlates of the brain's intrinsic large-scale functional architecture. Proc Natl Acad Sci U S A 105:16039-16044.
Jiang H, Bahramisharif A, van Gerven MA, Jensen O (2015) Measuring directionality between neuronal oscillations of different frequencies. Neuroimage 118:359-367.
Keller CJ, Bickel S, Honey CJ, Groppe DM, Entz L, Craddock RC, Lado FA, Kelly C, Milham M, Mehta AD (2013) Neurophysiological investigation of spontaneous correlated and anticorrelated fluctuations of the BOLD signal. J Neurosci 33:6333-6342.
Kenet T, Bibitchkov D, Tsodyks M, Grinvald A, Arieli A (2003) Spontaneously emerging cortical representations of visual attributes. Nature 425:954-956.
Klimesch W (1999) EEG alpha and theta oscillations reflect cognitive and memory performance: a review and analysis. Brain Res Brain Res Rev 29:169-195.
Koch SP, Werner P, Steinbrink J, Fries P, Obrig H (2009) Stimulus-induced and state-dependent sustained gamma activity is tightly coupled to the hemodynamic response in humans. J Neurosci 29:13962-13970.
Lakatos P, Shah AS, Knuth KH, Ulbert I, Karmos G, Schroeder CE (2005) An oscillatory hierarchy controlling neuronal excitability and stimulus processing in the auditory cortex. J Neurophysiol 94:1904-1911.
Lavenex P, Amaral DG (2000) Hippocampal-neocortical interaction: a hierarchy of associativity. Hippocampus 10:420-430.
Leopold DA, Murayama Y, Logothetis NK (2003) Very slow activity fluctuations in monkey visual cortex: implications for functional brain imaging. Cereb Cortex 13:422-433.
Liu X, Yanagawa T, Leopold DA, Fujii N, Duyn JH (2015) Robust Long-Range Coordination of Spontaneous Neural Activity in Waking, Sleep and Anesthesia. Cereb Cortex 25:2929-2938.
Miller KJ, Honey CJ, Hermes D, Rao RP, denNijs M, Ojemann JG (2014) Broadband changes in the cortical surface potential track activation of functionally diverse neuronal populations. Neuroimage 85 Pt 2:711-720.

(56) References Cited

OTHER PUBLICATIONS

Miller KJ, Leuthardt EC, Schalk G, Rao RP, Anderson NR, Moran DW, Miller JW, Ojemann JG (2007) Spectral changes in cortical surface potentials during motor movement. J Neurosci 27:2424-2432.

Pfurtscheller G, Lopes da Silva FH (1999) Event-related EEG/MEG synchronization and desynchronization: basic principles. Clin Neurophysiol 110:1842-1857.

Power JD, Barnes KA, Snyder AZ, Schlaggar BL, Petersen SE (2012) Spurious but systematic correlations in functional connectivity MRI networks arise from subject motion. Neuroimage 59:2142-2154.

Qian T, Zhou W, Ling Z, Gao S, Liu H, Hong B (2013) Fast presurgical functional mapping using task-related intracranial high gamma activity. J Neurosurg 119:26-36.

Raghavachari S, Kahana MJ, Rizzuto DS, Caplan JB, Kirschen MP, Bourgeois B, Madsen JR, Lisman JE (2001) Gating of human theta oscillations by a working memory task. J Neurosci 21:3175-3183.

Raichle ME (2009) A paradigm shift in functional brain imaging. J Neurosci 29:12729-12734.

Ramot M, Fisch L, Harel M, Kipervasser S, Andelman F, Neufeld MY, Kramer U, Fried I, Malach R (2012) A widely distributed spectral signature of task-negative electrocorticography responses revealed during a visuomotor task in the human cortex. The Journal of neuroscience : the official journal of the Society for Neuroscience 32:10458-10469.

Sauseng P, Klimesch W, Heise KF, Gruber WR, Holz E, Karim AA, Glennon M, Gerloff C, Birbaumer N, Hummel FC (2009) Brain oscillatory substrates of visual short-term memory capacity. Curr Biol 19:1846-1852.

Scholvinck ML, Leopold DA, Brookes MJ, Khader PH (2013) The contribution of electrophysiology to functional connectivity mapping. Neuroimage 80:297-306.

Sederberg PB, Kahana MJ, Howard MW, Donner EJ, Madsen JR (2003) Theta and gamma oscillations during encoding predict subsequent recall. J Neurosci 23:10809-10814.

Shulman GL, Fiez JA, Corbetta M, Buckner RL, Miezin FM, Raichle ME, Petersen SE (1997) Common Blood Flow Changes across Visual Tasks: II. Decreases in Cerebral Cortex. J Cogn Neurosci 9:648-663.

Smith SM, Fox PT, Miller KL, Glahn DC, Fox PM, Mackay CE, Filippini N, Watkins KE, Toro R, Laird AR, Beckmann CF (2009) Correspondence of the brain's functional architecture during activation and rest. Proceedings of the National Academy of Sciences of the United States of America 106:13040-13045.

Smith SM, Vidaurre D, Beckmann CF, Glasser MF, Jenkinson M, Miller KL, Nichols TE, Robinson EC, Salimi-Khorshidi G, Woolrich MW, Barch DM, Ugurbil K, Van Essen DC (2013) Functional connectomics from resting-state fMRI. Trends Cogn Sci 17:666-682.

Suffczynski P, Kalitzin S, Pfurtscheller G, Lopes da Silva FH (2001) Computational model of thalamo-cortical networks: dynamical control of alpha rhythms in relation to focal attention. Int J Psychophysiol 43:25-40.

Zielinski BA, Gennatas ED, Zhou J, Seeley WW (2010) Network-level structural covariance in the developing brain. Proceedings of the National Academy of Sciences of the United States of America 107:18191-18196.

\* cited by examiner

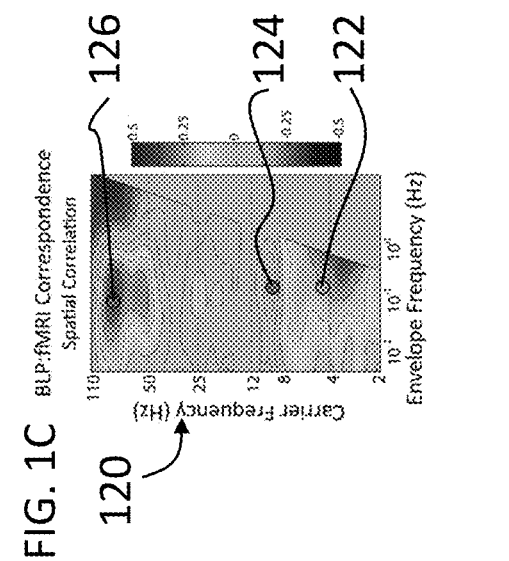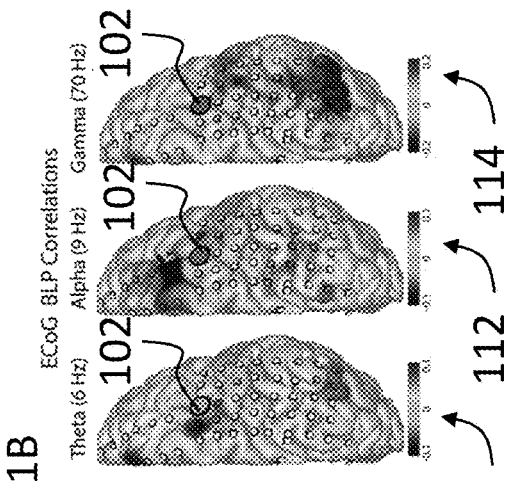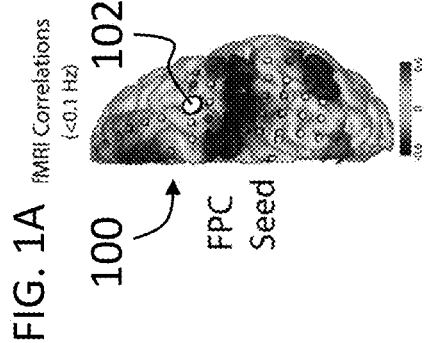
FIG. 1A  FIG. 1B  FIG. 1C
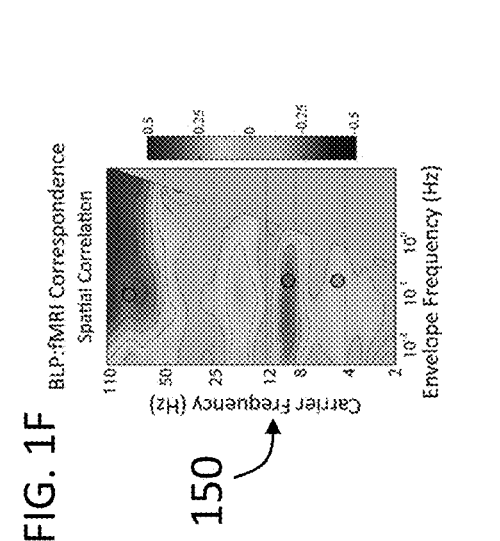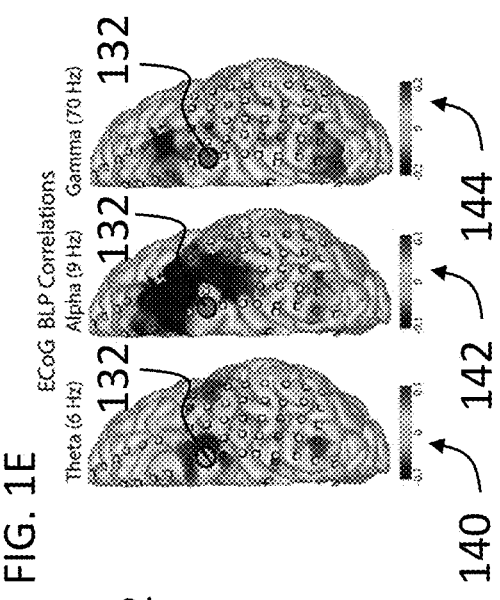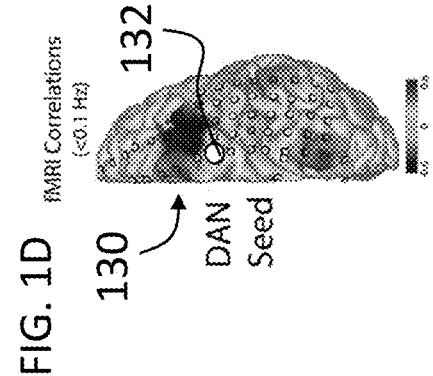
FIG. 1D  FIG. 1E  FIG. 1F

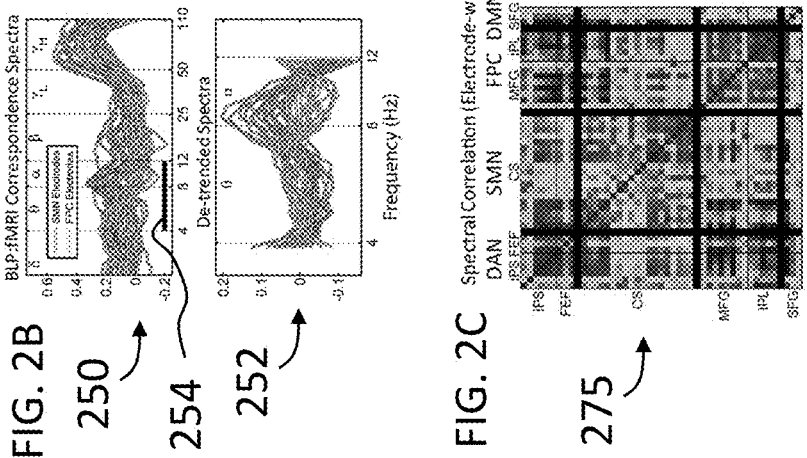
FIG. 2B
FIG. 2C
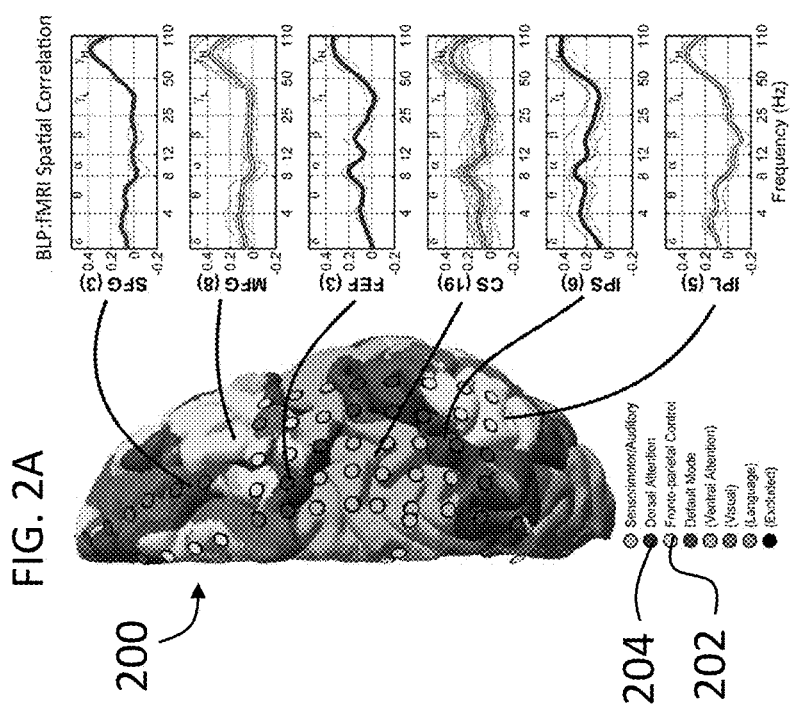
FIG. 2A

300

325

375

350

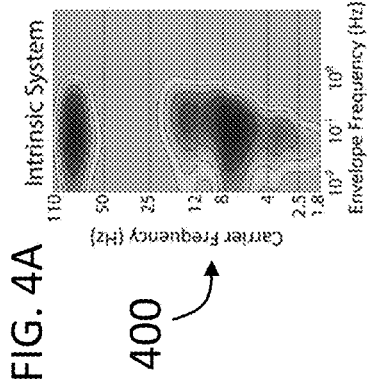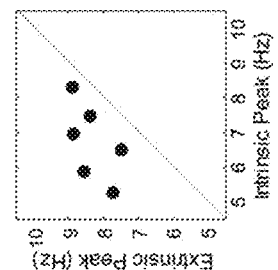
FIG. 4A — 400
FIG. 4B — 425
FIG. 4C — 450
FIG. 4D — 475

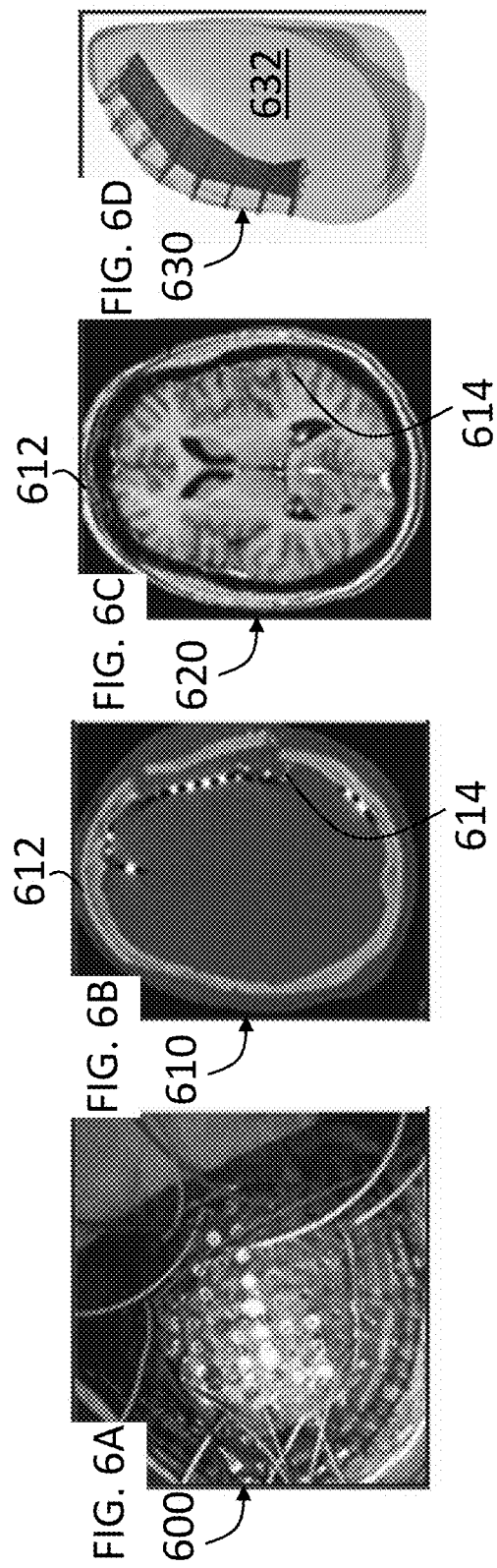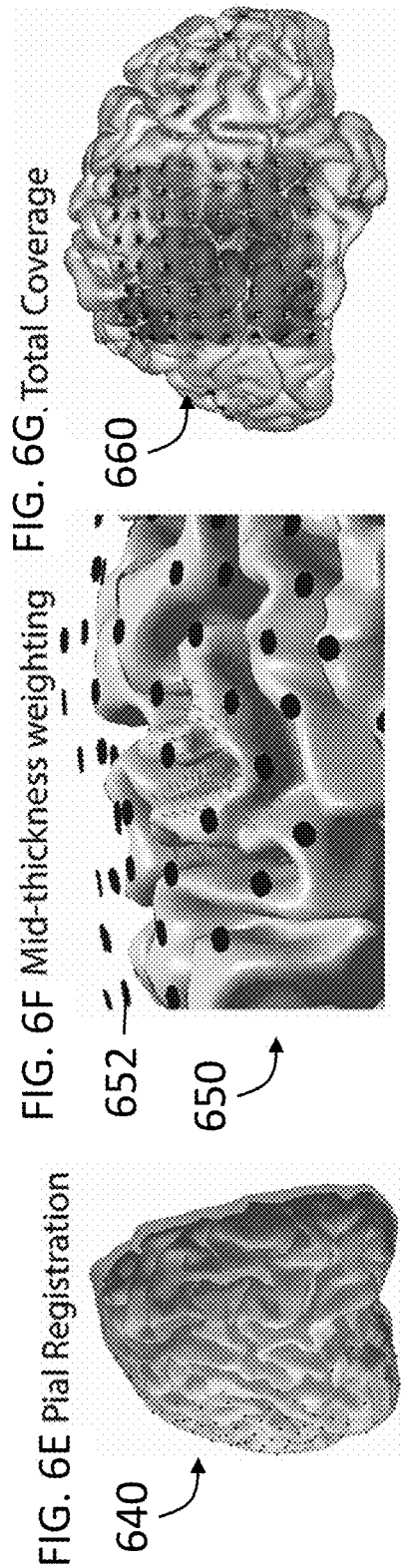

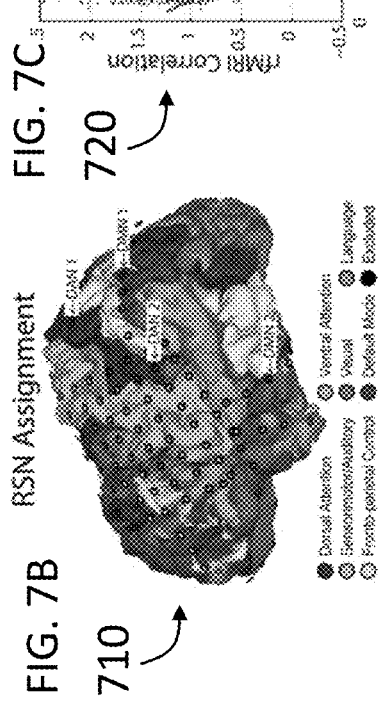
FIG. 7A fMRI on Electrodes - $f_e(t)$
700
FIG. 7B RSN Assignment
710
FIG. 7C
720
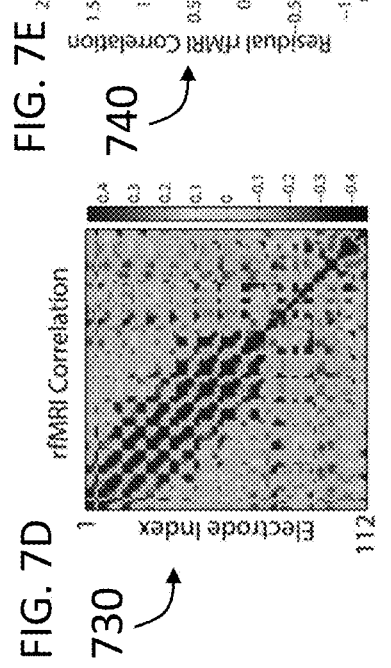
FIG. 7D
730
FIG. 7E
740
FIG. 7F Residual rfMRI Correlation
750

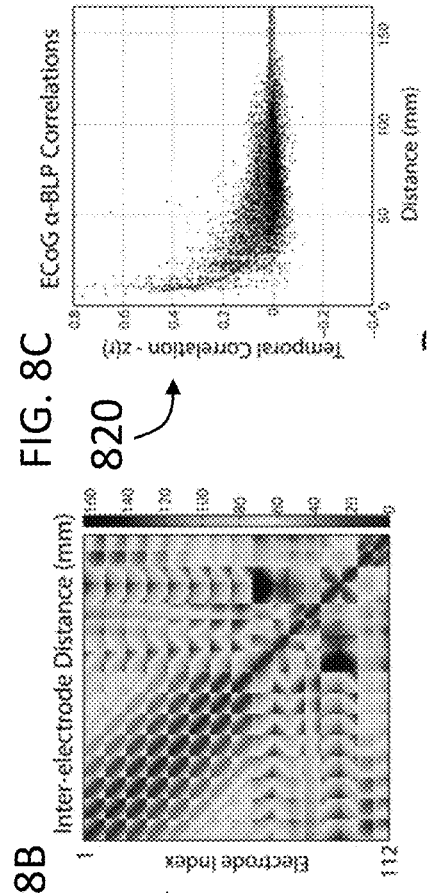
FIG. 8A 800
FIG. 8B 810
FIG. 8C 820
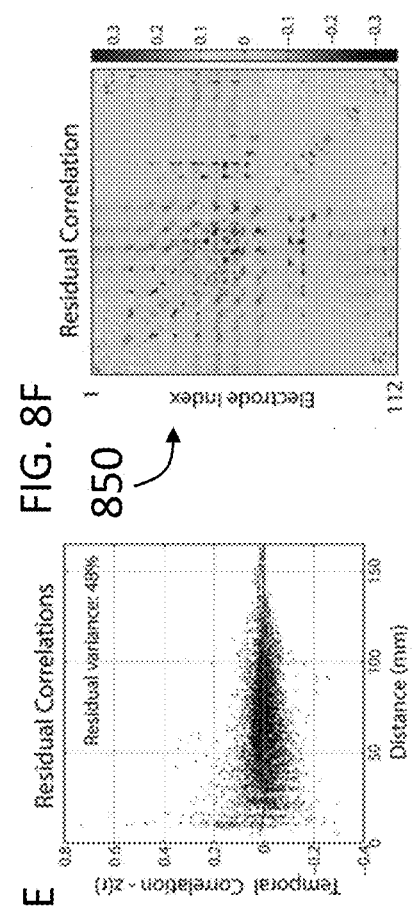
FIG. 8D 830
FIG. 8E 840
FIG. 8F 850

DEPRESSION BRAIN COMPUTER INTERFACE FOR THE QUANTITATIVE ASSESSMENT OF MOOD STATE AND FOR BIOFEEDBACK FOR MOOD ALTERATION

CROSS REFERENCE TO RELATED APPLICATIONS

This application claims priority to U.S. Provisional Application Ser. No. 62/280,368, filed Jan. 19, 2016, the entire disclosure of which is hereby incorporated by reference in its entirety.

STATEMENT REGARDING FEDERALLY SPONSORED RESEARCH OR DEVELOPMENT

This invention was made with government support under Grant P30NS048056 awarded by the National Institute of Health (NIH). The government may have certain rights in the invention

FIELD OF THE DISCLOSURE

The present disclosure is generally directed to mood state and, more particularly, to using an electroencephalogram (EEG) headset to evaluate neurologic network interactions.

BACKGROUND OF THE DISCLOSURE

Intrinsic brain activity has emerged as a focus of systems neuroscience research. Resting state, i.e., task-free, functional magnetic resonance imaging (R-fMRI) currently is one technique used in the investigation of intrinsic brain activity. Based on R-fMRI studies, slow (less than 0.1 Hz), intrinsic fluctuations of the blood oxygen level dependent (BOLD) signal are temporally correlated within spatially distributed functional systems whose topography recapitulates patterns of activity during active behavior. The associated topographies are known as resting state networks (RSNs) or, equivalently, intrinsic connectivity networks (ICNs).

Although it is generally assumed that there exist electrophysiological correlates of RSNs, the fundamental nature of these relations remains uncertain. Electrocorticographic (ECoG) recording on the surface of the brain provides a means of studying the electrophysiologic correlates of RSNs at a temporal resolution inaccessible to fMRI. Task-based studies in primates as well as humans suggest that the robust electrophysiological correlate of the BOLD fMRI signal is wide band power, nominally in the range of 40-150 Hz. This principle has been assumed to extend to the resting state. Prior resting state ECoG studies demonstrate a correspondence between gamma (nominally, 70-110 Hz) band-limited power (BLP) timeseries correlations and R-fMRI RSNs. However, correspondence of BLP timeseries correlations to fMRI RSNs has so far not been systematically evaluated at lower frequencies.

A fundamental property of fMRI RSNs is that they are hierarchically organized and that their nested structure is divided at the highest level between two 'systems', often referred to as the "extrinsic" vs. "intrinsic" systems. The intrinsic system is related to episodic memory, executive control, and social cognition, whereas the extrinsic system instantiates spatial attention and sensory-motor interactions with the environment. It has been observed that, both at rest and during task performance, these systems are negatively coupled. This negative coupling has been interpreted as reflecting reciprocal inhibition between externally vs. internally directed cognition.

Electrophysiology experiments have identified oscillatory responses specifically associated with "extrinsic" vs. "intrinsic" functions: alpha (8-12 Hz) power is suppressed during performance of motor and perceptual/attentional tasks, i.e., extrinsic functions, whereas theta (4-8 Hz) power is induced by executive control, working memory and episodic memory tasks, i.e., intrinsic functions. Thus, the systems instantiating distinct cognitive functions generate task-induced electrophysiological responses with separable spectral content.

BRIEF DESCRIPTION

In one aspect, a brain computer interface (BCI) system includes an electroencephalogram (EEG) headset and a computing device communicatively coupled to the EEG headset. The computing device includes a memory, a processor and a display device. The memory stores instructions that, when executed by the processor, cause the processor to monitor, using the EEG headset, current extrinsic network activity and current intrinsic network activity of a patient, generate a current depression index based on the relationship between the current extrinsic network activity and the current intrinsic network activity, and display, on the display device, a representation of the relationship between the current depression index and a baseline depression index previously generated for the patient.

In another aspect, a method of using a BCI system including an EEG headset, a display device, and a computing device communicatively coupled to the EEG headset and the display device is provided. The method is at least partially performed by the computing device. The method includes monitoring current extrinsic network activity and current intrinsic network activity of a patient and generating a current depression index based on the relationship between the current extrinsic network activity and the current intrinsic network activity.

In yet another aspect, a mobile communications device includes a headset removably attached to the mobile communications device, a processor, a display device, and a memory. The headset includes at least one speaker to output audio from the mobile communications device, a band positioned adjacent a head of a patient, and a plurality of EEG electrodes coupled to the band. The memory stores instructions that, when executed by the processor, cause the processor to monitor, using the plurality of EEG electrodes, current extrinsic network activity and current intrinsic network activity of the patient, generate a current depression index based on the relationship between the current extrinsic network activity and the current intrinsic network activity, and display, on the display device, a representation of the relationship between the current depression index and a baseline depression index previously generated for the patient.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A depicts a seed-based functional magnetic resonance image (fMRI) correlation map for a seed region within the fronto-parietal control system (FPC).

FIG. 1B depicts a seed-based electrocorticographic (ECoG) band-limited power (BLP) correlation maps for the seed region shown in FIG. 1A.

FIG. 1C depicts a quantitative summary of the spatial correlation findings of FIGS. 1A and 1B.

FIG. 1D illustrates a seed-based fMRI correlation map for a seed region within the dorsal attention network (DAN).

FIG. 1E depicts a seed-based ECoG BLP correlation maps for the seed region shown in FIG. 1D.

FIG. 1F depicts a quantitative summary of the spatial correlation findings of FIGS. 1D and 1E.

FIG. 2A illustrates a diagram of resting state network (RSN) nodes defined within-subject by supervised classification of fMRI signal correlation patterns.

FIG. 2B depicts a first plot of correspondence spectra aggregated over sensorimotor (SMN) and FPC networks and a second plot of correspondence spectra after linear detrending.

FIG. 2C illustrates a plot of correspondence spectrum similarity across electrode pairs computed by linear correlation over the 4-13 Hz range.

FIG. 4A depicts a plot of correspondence spectrum averaged across all electrodes overlying intrinsic system RSNs.

FIG. 4B depicts a plot of correspondence spectrum average for all extrinsic system electrodes similar to the plot shown in FIG. 4A.

FIG. 4C includes a plot of correspondence spectra collapsed over the 0.1-1 Hz modulation frequency range for both intrinsic and extrinsic systems.

FIG. 4D depicts a plot of peak frequencies for individual within-subject system averages.

FIG. 6A depicts an intraoperative photo taken at the time of electrode grid and strip implantation of an example experiment.

FIG. 6B depicts co-registration of a post-operative CT image.

FIG. 6C depicts the co-registration shown in FIG. 6B with a pre-operative structural MRI.

FIG. 6D illustrates a diagram of a pial surface.

FIG. 6E depicts a diagram of segmented electrode coordinates after projection to a smoothed pial surface.

FIG. 6F depicts a diagram of electrode models (overlaid on a mid-thickness surface.

FIG. 6G illustrates a diagram of a sum of weight functions across all electrodes.

FIG. 7A depicts a plot of an estimate of RSN identity of each surface locus in an individual based on supervised classification of seed-based blood oxygen level dependent (BOLD) correlation maps.

FIG. 7B depicts a diagram of exemplar BOLD time-series after sampling surface-processed time-series to electrodes using the weight function described in FIGS. 6A-6G.

FIG. 7C depicts a temporal correlation matrix of BOLD signals between all pairs of electrodes after spline regression of distance-related correlation trends.

FIG. 7D depicts a plot of rfMRI correlation with an electrode index.

FIG. 7E depicts a plot of residual rfMRI correlation with distance.

FIG. 7F depicts another plot of rfMRI correlation with an electrode index.

FIG. 8A depicts a plot of 10 Hz signals filtered from two exemplar channels.

FIG. 8B depicts a plot of Euclidean distance across all pairs of electrodes.

FIG. 8C depicts a plot of a relationship of correlation values to electrode distance in raw data with a two parameter fit.

FIG. 8D depicts a plot of pairwise temporal correlation between electrodes corresponding to the plot shown in FIG. 8C.

FIG. 8E depicts a plot of temporal correlations after re-referencing data to a common average.

FIG. 8F depicts a plot of residual correlations after re-referencing data to a common average.

DETAILED DESCRIPTION

The present disclosure is directed toward systems and methods for generating quantitative feedback associated with mood using intrinsic and extrinsic brain activity. The large-scale spatial topography of spontaneous temporal correlations computed with ECoG and fMRI signals are compared. This comparison is evaluated across ECoG frequencies and brain regions to test the hypothesis that the frequencies of maximal ECoG:fMRI correspondence are specific to the extrinsic vs. intrinsic systems.

In the example embodiment, a brain computer interface (BCI) system includes a sensing device and a computing device in communication with the sensing device. The sensing device is an electroencephalogram (EEG) headset that includes a plurality of electrodes. The EEG headset is worn by a patient to collect measurements associated with brain activity using the electrodes. In particular, the electrodes collect measurements associated with intrinsic brain activity and extrinsic brain activity. The measurements are transmitted to the computing device for analysis and presentation. The computing device is configured to compare the measurements to determine the patient's mood based on a previously determined baseline brain activity associated with the patient. That is, the brain activity associated with the patient's current mood is compared to a baseline mood of the patient that was previously determined to analyze changes to the patient's mood. The computing device is configured to present a representation of the relationship between the patient's current mood and the baseline mood to the patient and/or another user (e.g., a doctor). The BCI system may be used to analyze the effectiveness of a particular mood intervention treatment or to analyze the patient's mood over a period of time. In at least some embodiments, the computing device is a mobile device associated with the patient such that the patient is presented information.

Figure 9:
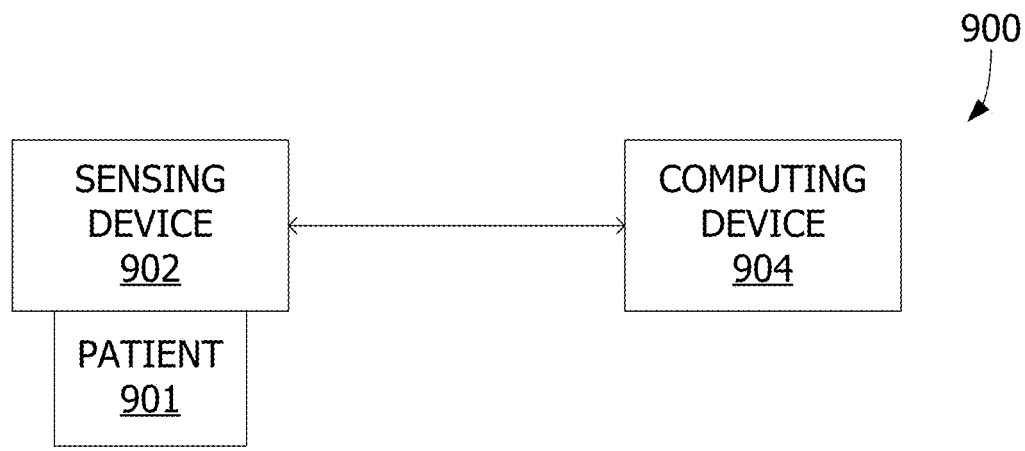
FIG. 9 is a block diagram of an example brain computing interface (BCI) system for measuring an analyzing intrinsic and extrinsic brain activity.

FIG. 9 is a block diagram of an example BCI system 900 for collecting and analyzing extrinsic and intrinsic network activity of a patient 901. In the example embodiment, system 900 includes a sensing device 902 and a computing device 904. In other embodiments, system 900 includes additional, fewer, or alternative components, including those described elsewhere herein.

Sensing device 902 is configured to detect a plurality of measurements of brain activity that is representative of intrinsic and extrinsic brain activity as described herein. In the example embodiment, sensing device 902 is an EEG headset worn by patient 901. The EEG headset may be an audio headset for playing sound from computing device 904 and/or another computing device (not shown). For example, sensing device 902 may include at least one speaker to output audio from computing device 904 and a band configured to be positioned adjacent a head of a patient. In other embodiments, sensing device 902 may be a different device suitable to collect measurements of intrinsic and extrinsic brain activity. It should be noted that the present disclosure is not limited to any one particular type of imaging and electrical technique or device, and one of ordinary skill in the art will appreciate that the current disclosure may be used in connection with any type of technique or device that enables system 900 to function as described herein.

In the example embodiment, sensing device 902 includes a plurality of electrodes 903 to collect the measurements for patient 901. In some embodiments, sensing device 902 is non-invasive (i.e., EEG) such that electrodes 903 are integrated within sensing device 102 and worn by patient 901. In other embodiments, electrodes 903 are implanted on the head of patient 901 (i.e., ECoG) such that sensing device 902 collects the measurements from electrodes 903 when patient 901 wears sensing device 902. Electrodes 903 are spaced apart to collect data from different regions of the brain of patient 901.

Computing device 904 is coupled to sensing device 902 via a data conduit 906. It should be noted that, as used herein, the term "couple" is not limited to a direct mechanical, electrical, and/or communication connection between components, but may also include an indirect mechanical, electrical, and/or communication connection between multiple components. Sensing device 902 may communicate with computing device 904 using a wired network connection (e.g., Ethernet or an optical fiber), a wireless communication means, such as radio frequency (RF), e.g., FM radio and/or digital audio broadcasting, an Institute of Electrical and Electronics Engineers) (IEEE®) 802.11 standard (e.g., 802.11(g) or 802.11(n)), the Worldwide Interoperability for Microwave Access (WIMAX®) standard, a short-range wireless communication channel such as BLUETOOTH®, a cellular phone technology (e.g., the Global Standard for Mobile communication (GSM)), a satellite communication link, and/or any other suitable communication means. IEEE is a registered trademark of the Institute of Electrical and Electronics Engineers, Inc., of New York, N.Y. WIMAX is a registered trademark of WiMax Forum, of Beaverton, Oreg. BLUETOOTH is a registered trademark of Bluetooth SIG, Inc. of Kirkland, Wash.

In the exemplary embodiment, computing device 904 is configured to receive at least one signal representative of a plurality of measurements of intrinsic and extrinsic brain activity from sensing device 902. More specifically, computing device 904 is configured to receive at least one signal representative of at least one voltage or frequency fluctuation within the brain from at least one electrode.

Computing device 904 is configured to analyze the intrinsic brain activity and the extrinsic brain activity of patient 901 from the signal(s) from sensing device 902 to generate a depression index (i.e., a mood index) for patient 901. That is, computing device 904 establishes a baseline depression index of intrinsic and extrinsic brain activity for patient 901 and stores the baseline depression index. Subsequent intrinsic and extrinsic brain activity (also referred to as the "current depression index") may be compared to the baseline depression index to determine the relative mood of patient 901. For example, a comparison may be made prior to and after therapy or medical treatment for mood intervention to quantify the effect of the therapy or treatment.

Computing device 904 is further configured to display or otherwise present the depression index and/or other data generated from the signal of sensing device 902 to patient 901 or another user (e.g., a doctor). In the example embodiment, computing device 904 is configured to display an interactive environment with the depression index for patient 901 and/or another user to view. In at least some embodiments, the intrinsic and extrinsic brain activity is provided as biofeedback.

In some embodiments, computing device 904 is a portable computing device, such as, but not limited to, a portable communications device (such as a smartphone), wearable device, tablet, portable music player, or laptop. In such embodiments, computing device 904 may store an application or other software module associated with system 900. The application may be used to record and process the signal from sensing device 902, analyze the data, and provide any feedback to the user (e.g., patient 901). The application may be configured to "gamify" the use of system 900. That is, the application may provide an interactive environment of challenges and/or incentives to patient 901 to use system 900. The interactive environment is responsive to the monitored intrinsic and extrinsic brain activity or an index derived therefrom. In other embodiments, computing device 904 is a different computing device, such as a desktop computing device. In certain embodiments, computing device 904 includes a plurality of computing devices communicatively coupled together, such as cloud computing and/or other distributed computing systems, to perform the functions of computing device 904 as described herein.

Figure 10:
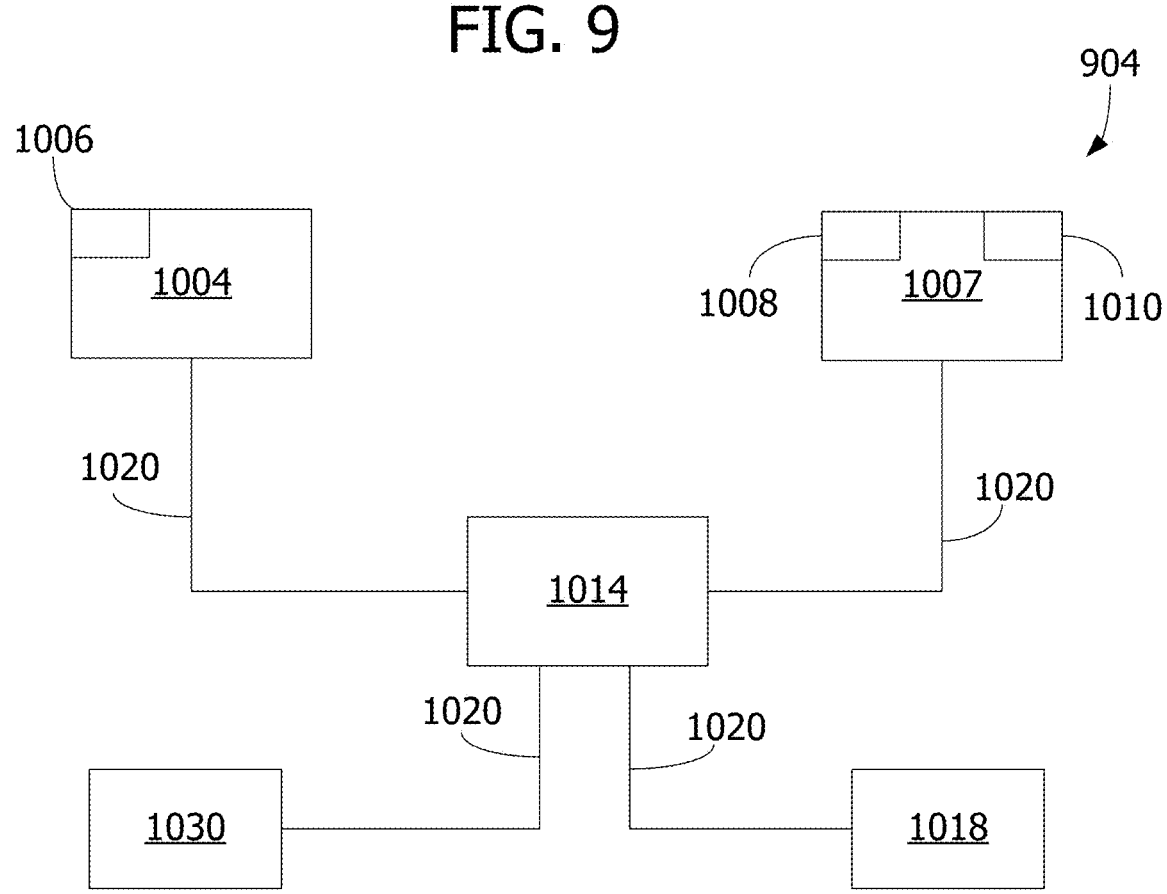
FIG. 10 is a block diagram of an example computing device that may be used with the system shown in FIG. 9.

FIG. 10 is a block diagram of computing device 904. In the exemplary embodiment, computing device 904 includes a user interface 1004 that receives at least one input from a user, such as an operator of sensing device 902 (shown in FIG. 9). User interface 1004 may include a keyboard 1006 that enables the user to input pertinent information. User interface 1004 may also include, for example, a pointing device, a mouse, a stylus, a touch sensitive panel (e.g., a touch pad, a touch screen), a gyroscope, an accelerometer, a position detector, and/or an audio input interface (e.g., including a microphone).

Moreover, in the exemplary embodiment, computing device 904 includes a presentation interface 1007 that presents information, such as the Depression Index, to the user. Presentation interface 1007 may also include a display adapter 1008 that is coupled to at least one display device 1010. More specifically, in the exemplary embodiment, display device 1010 may be a visual display device, such as a cathode ray tube (CRT), a liquid crystal display (LCD), an organic LED (OLED) display, and/or an "electronic ink" display. Alternatively, presentation interface 1007 may include an audio output device (e.g., an audio adapter and/or a speaker) and/or a printer.

Computing device 904 also includes a processor 1014 and a memory device 1018. Processor 1014 is coupled to user interface 1004, presentation interface 1007, and to memory device 1018 via a system bus 1020. In the exemplary embodiment, processor 1014 communicates with the user, such as by prompting the user via presentation interface 1007 and/or by receiving user inputs via user interface 1004. The term "processor" refers generally to any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, memory device 1018 includes one or more devices that enable information, such as executable instructions and/or other data, to be stored and retrieved. Moreover, memory device 1018 includes one or more computer readable media, such as, without limitation, dynamic random access memory (DRAM), static random access memory (SRAM), a solid state disk, and/or a hard disk. In the exemplary embodiment, memory device 1018 stores, without limitation, application source code, application object code, configuration data, additional input events, application states, assertion statements, validation results, and/or any other type of data. Computing device 904, in the exemplary embodiment, may also include a communication interface 1030 that is coupled to processor 1014 via system bus 1020. Moreover, communication interface 1030 is communicatively coupled to sensing device 902.

An example experiment was conducted using system 900 (shown in FIG. 9). To enable direct comparison of resting state ECoG vs. BOLD fMRI temporal correlations, preprocessed fMRI timeseries (see Experimental Procedures below) were projected onto the brain surface and resampled at electrode loci (see FIGS. 6A-6G and 7A-7F). ECoG signals were referenced to the common mean (excluding noisy and ictal electrodes) and band-pass filtered at logarithmic intervals to isolate particular carrier frequencies; these band-limited signals were squared and then filtered to isolate specific modulation frequencies of the BLP signal derived from a given carrier frequency band (see Experimental Procedures below for further details). Pearson product-moment temporal correlations were computed for all electrode pairs, treating the fMRI and ECoG BLP timeseries identically. ECoG:fMRI correspondence was computed as the spatial correlation of the ECoG BLP temporal correlations and fMRI temporal correlations. Thus, for each seed electrode, the ECoG:fMRI correspondence spectrum was assessed as a function BLP carrier and modulation frequency.

FIGS. 1A-1F depict spatial correspondence of ECoG and fMRI correlation maps in a single subject based on measurements collected by sensing device 902 (shown in FIG. 9). More specifically, FIG. 1A depicts a seed-based fMRI correlation map 100 for a seed region 102 within the fronto-parietal control system (FPC). The correlation map 100 rendering is limited to regions with electrode coverage. The fMRI correlation map 100 is obtained with a seed electrode overlying the middle frontal gyrus, a locus within the fronto-parietal control RSN, which is a component of the intrinsic system. Positive correlation is observed with signals in lateral parietal cortex (frontoparietal control network) and superior frontal cortex (default mode), and negative correlation with precentral/postcentral cortex (motor), and intraparietal sulcus (dorsal attention).

FIG. 1B depicts seed-based ECoG BLP correlation maps 110, 112, and 114 for the same seed region 102 as shown in FIG. 1A. The corresponding ECoG BLP seed-based correlation maps 110, 112, 114 are obtained with the same seed at different carrier frequencies. As is evident in FIGS. 1A and 1B, the topography of theta and gamma but not alpha BLP correlations was spatially similar to the topography BOLD fMRI temporal correlations.

FIG. 1C depicts a quantitative summary of the findings of FIGS. 1A and 1B, including a plot 120 of ECoG:fMRI correspondence assessed by spatial correlation of correlation maps 100, 110, 112, and 114, parametric in ECoG BLP carrier and modulation frequencies. Circles 122, 124, 126 indicate frequencies for exemplars in maps 110, 112, 114, respectively. Note that ECoG correlation maps 110, 114 for theta and gamma frequencies for this seed region 102 in FIG. 1B are similar to the fMRI correlation map 100 in FIG. 1A. Plot 120 shows the ECoG:fMRI correspondence spectrum (across carrier×modulation frequencies). ECoG:fMRI correspondence was modestly dependent on modulation frequency but strongly dependent on carrier frequency. Thus, BLP spectral specificity appears in the carrier×modulation display as broad horizontal bands with peaks within the high gamma (50-100 Hz) and theta bands (4-8 Hz).

FIGS. 1D-1F illustrate results, similar to FIGS. 1A, 1B, and 1C, respectively, for a seed region 132 in the dorsal attention network (DAN). Note that correlation maps 142 and 144 for the DAN seed 132 at alpha (rather than theta) and gamma frequencies are similar to the fMRI correlation map 130 in FIG. 1D. The frequency specific ECoG:fMRI similarity produces complimentary peaks of spatial correlation in the theta and alpha ranges in plots 120 and 150, respectively. The results of FIGS. 1D-1F are complementary to the results of FIGS. 1A-1C, and are obtained with an electrode seed overlying the frontal eye field (FEF), a locus within the dorsal attention RSN, a component of the extrinsic system. This locus showed strong ECoG:fMRI correspondence with alpha (8-12 Hz) and gamma but not theta frequencies. Thus, both seeds exhibited similar resting state BOLD fMRI and BLP correlation topographies at high gamma frequencies. Intrinsic vs. extrinsic spectral specificity was observed at theta and alpha BLP frequencies, respectively.

FIGS. 2A-2C illustrate ECoG:fMRI correspondence spectra vary according to RSN. The results shown in FIGS. 2A-2C are for the same subject as FIGS. 1A-1F. FIG. 2A illustrates a diagram 200 of RSN nodes defined within-subject by supervised classification of fMRI signal correlation patterns. In addition, ECoG:fMRI correspondence spectra are averaged across electrodes within each node (traces: individual electrodes, thick line: within-node electrode average). FIG. 2B depicts a first plot 250 of correspondence spectra aggregated over SMN and FPC networks and a second plot 252 of correspondence spectra after linear detrending. Note a predominance FPC peaks at 6 Hz and SMN peaks at 9 Hz. A black bar 254 indicates a range of frequencies used to compute correlations in FIG. 2C. FIG. 2C illustrates a plot 275 of correspondence spectrum similarity across electrode pairs computed by linear correlation over the 4-13 Hz range. The abbreviations shown in FIG. 2C are as follows: SFG is superior frontal gyrus (DMN); MFG is middle frontal gyrus (FPC); FEF is frontal eye field (DAN); CS is central sulcus (SMN); IPS is intraparietal sulcus (DAN); and IPL is inferior parietal lobule (DAN).

FIGS. 2A-2C extend the analysis shown in FIGS. 1A-1F to include all electrodes for one subject. The cortical surface was parcellated into seven predefined RSNs. Thus, each electrode was assigned to one node of one RSN. Correspondence spectra were averaged across electrodes within each node. RSNs generally are comprised of spatially discontinuous regions (nodes). For example, the fronto-parietal control (FPC) RSN includes five distinct nodes within a first cortical surface (including all regions shaded as indicated by reference numeral 202). Thus, each electrode was assigned to one node of one RSN. Correspondence spectra were averaged across electrodes within each node. The results of this analysis (FIG. 2B) reveal the dependence of ECoG:fMRI correspondence on RSN. High correspondence in the gamma frequency range (nominally, above 45 Hz) and upper gamma range (nominally, above 50 Hz) is ubiquitous. Low correspondence is generally observed in the beta frequency range (nominally, 13-45 Hz) and/or the low-gamma frequency range (nominally, 25-50 Hz). At lower BLP frequencies, the frequency of maximal correspondence depends on RSN. Thus, components of the dorsal attention network (DAN; indicated by reference numeral 204) exhibit high correspondence in the low-alpha range (8-10 Hz), whereas components of the fronto-parietal control (FPC; indicated by reference numeral 202) RSN exhibit maximal correspondence in the theta range (4-8 Hz).

The results suggest that the fine features (i.e., locations of peaks and troughs) of ECoG:fMRI correspondence spectra differ according to RSN in the 4-13 Hz range. To quantitate this observation, a numerical index of correspondence spectrum similarity for all electrode pairs was computed in the experiment. Specifically, the correspondence spectrum at each electrode was detrended as illustrated in plot 252 of FIG. 2B and the Pearson correlation was computed over logarithmic frequency bins in the 4-13 Hz range. The electrode-pair matrix result, shown in plot 275 of FIG. 2C, demonstrates similarity of spectral features at the highest level of the RSN hierarchy. Thus, high similarity was found between all electrodes within the DAN and the sensorimotor network (SMN; extrinsic system). High similarity was found between all electrodes within the FPC and the default mode network (DMN; intrinsic system). In contrast, low similarity was found for electrodes paired on opposite poles of the hierarchy, e.g., DAN:DMN.

Figure 3A:
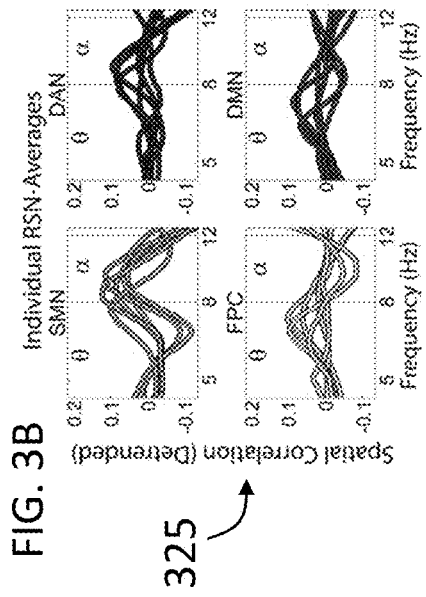
FIG. 3A depicts a plot of ECoG:fMRI correspondence spectra averaged within RSNs across all electrodes and all subjects of an example experiment.
Figure 3B:
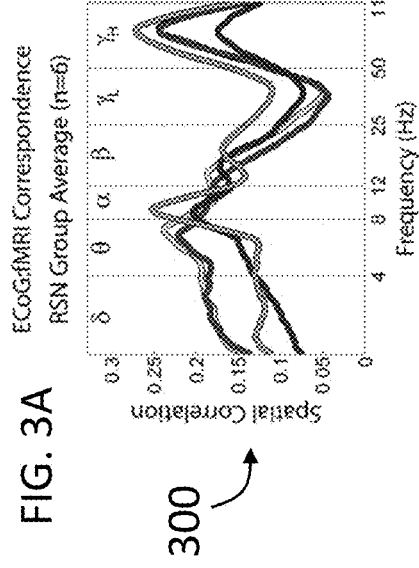
FIG. 3B depicts a plot of detrended ECoG:fMRI spatial correlation spectra averaged within RSNs.
Figure 3D:
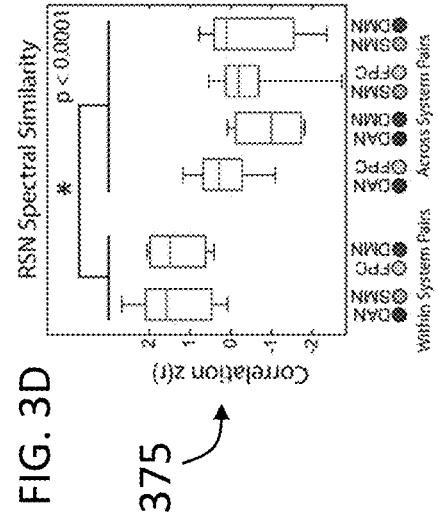
FIG. 3D depicts a chart of distributions of inter-RSN spectral correlations over the subjects.
Figure 3C:
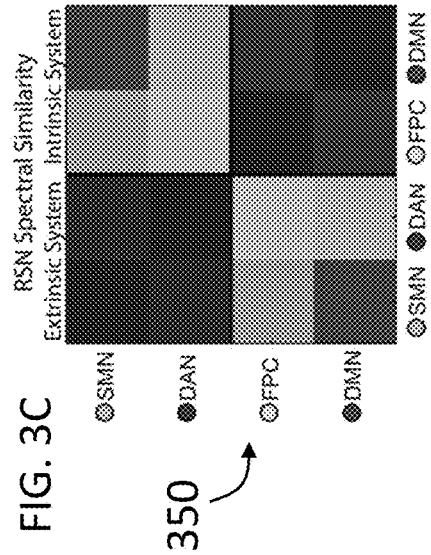
FIG. 3C depicts a plot of correlation between RSN-averaged detrended spectra shown in FIG. 3B that have been averaged across the subjects.

FIGS. 3A-3D illustrate the extrinsic vs. intrinsic system dichotomy of a second example experiment using system 900 (shown in FIG. 9). FIG. 3A includes a plot 300 of ECoG:fMRI correspondence spectra averaged within RSNs across all electrodes and all subjects. FIG. 3B depicts a plot 325 of detrended ECoG:fMRI spatial correlation spectra averaged within RSNs. Each trace corresponds to an individual participant. FIG. 3C depicts a plot 350 of correlation between RSN-averaged detrended spectra shown in plot 325, averaged across participants. Higher correlation indicates greater similarity of RSN-specfic spectral features. FIG. 3D depicts a chart 375 of distributions of inter-RSN spectral correlations over subjects. Within each box plot the line indicates the inter-subject median, the box indicates inter-quartile range, and the whiskers indicate range.

To examine the extrinsic vs. intrinsic system dichotomy at the group level, ECoG:fMRI correspondence spectra were averaged over electrodes within RSNs in six subjects using computing device 904 (shown in FIG. 9). Averaged RSN-specific spectra in plot 300 revealed system-specific features. The extrinsic system (DAN and SMN) mean spectrum peaked at 9 Hz. The intrinsic system (DMN and FPC) mean spectrum peaked at 7 Hz. These differences in peak loci also were consistently obtained at the single subject level by averaging detrended correspondence spectra over electrodes within each RSN (see plots 350 and 375). The similarity of RSN-specific spectra within and across systems was evaluated for each subject as the Fisher z-transformed Pearson correlation over log frequency spanning 4-13 Hz. The spectral similarity measures then were averaged over subjects to obtain the group-level results shown in plot 350. These results reveal a block structure corresponding to the extrinsic vs. intrinsic system dichotomy. Distributions over subjects of the RSN:RSN similarity measures are shown in chart 375. Within-system correlations (average of DAN:SMN and FPC:DMN) were systematically higher than across-system correlations (average of DAN:DMN, DAN:FPC, SMN:DMN, and SMN:FPC for $p<0.0001$, one sided t-test).

FIGS. 4A-4D illustrate system-level spectral specificity of ECoG correlations determined by computing device 904 (shown in FIG. 9). FIG. 4A depicts a plot 400 of correspondence spectrum averaged across all electrodes overlying intrinsic system RSNs (average over all subjects). Spectral features in the carrier domain were similar to exemplar in plot 120 (shown in FIG. 1C). FIG. 4B depicts a plot 425 of correspondence spectrum average for all extrinsic system electrodes in the same format as plot 400. Note similarity to plot 150 (shown in FIG. 1F). Also note that plots 400 and 425 exhibit a gamma peak at the same frequency, but different peaks for low frequencies: 9-10 Hz for the extrinsic system average in plot 425 and 6-7 Hz for the intrinsic system average in plot 400. FIG. 4C includes a plot 450 of correspondence spectra collapsed over the 0.1-1 Hz modulation frequency range for both systems. Note offset of peaks in the theta and alpha range. FIG. 4D depicts a plot 475 of peak frequencies for individual within-subject system averages. Each marker represents the peak frequency in the 4-13 Hz range for one subject.

FIGS. 4A-4D show extrinsic and intrinsic system correspondence spectra averaged over all subjects. These results demonstrate, at the group level, the principle features illustrated in FIGS. 1A-1F: ECoG:fMRI correspondence depends only modestly on modulation frequency but is sharply structured in relation to carrier frequency (plots 400 and 425). The extrinsic and intrinsic systems both exhibit high ECoG:fMRI correspondence in the gamma (greater than 50 Hz) carrier frequency range and a trough at approximately 35 Hz (plot 450). Most importantly, extrinsic vs. intrinsic carrier specificity is most marked in the 4-13 Hz range, i.e., in the theta and alpha bands.

Figures 5A, 5B:
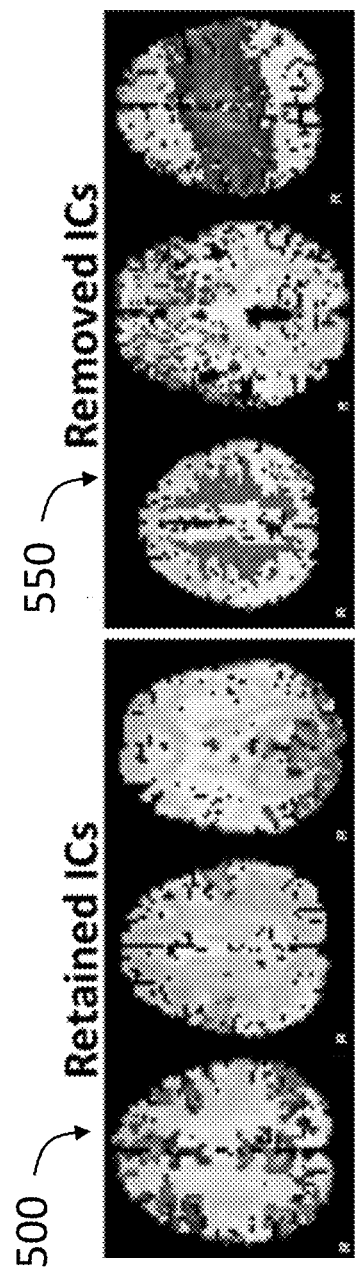
FIG. 5A depicts a set of scans of components of neuronal origin.
FIG. 5B depicts a set of scan of artifact components of physiologic or non-physiologic origin.

FIGS. 5A and 5B illustrate exemplar manually classified ICA components. FIG. 5A depicts a set of scans 500 of components of neuronal origin (i.e., resting state network components). FIG. 5B depicts a set of scan 550 of artifact components of physiologic (e.g., respiratory, cardiac) or non-physiologic (e.g., head motion) origin.

FIGS. 6A-6G illustrate co-registration of electrodes with brain surface. FIG. 6A depicts an intraoperative photo 600 taken at the time of electrode grid (i.e., electrodes 903, shown in FIG. 9) and strip implantation. FIGS. 6B and 6C depict co-registration of a post-operative CT image 610 (FIG. 6B) with a pre-operative structural MRI 620 (FIG. 6C). Electrode artifacts can be plainly seen in the CT image 610. The outline 612 was auto-traced on the CT image 610 and transferred to the structural MRI 620 to verify the co-registration. Note that the electrode at the posterior skull osteotomy is deep relative to the inner table of the skull (indicated by bar 614). This distortion leads to electrode coordinates recovered inside the brain in the undistorted, pre-operative MRI 620. FIG. 6D illustrates a diagram 630 of a pial surface 632. The distortion described above is corrected by projecting electrodes to a heavily smoothed pial surface 632 along a vector normal to the local surface of the grid. FIG. 6E depicts a diagram 640 of segmented electrode coordinates after projection to the smoothed pial surface 632. FIG. 6F depicts a diagram 650 of electrode models 652 (registered to pial surface 632) overlaid on mid-thickness surface. The surface sampling function for each electrode was defined as the inverse square of the distance from each electrode surface locus ($\vec{r}_e$) to each mid cortical thickness surface locus ($\vec{r}_{mid}$). The relative weighting function for an individual electrode (after integrating over the electrode surface, $\vec{r}_e$) is indicated by the surface hue or shade. Note that the contribution to each electrode is strongly local. FIG. 6G illustrates a diagram 660 of a sum of weight functions across all electrodes. This computation is not used for analyses, but is presented here to illustrate electrode coverage.

FIGS. 7A-7F illustrate computation by computing device 904 (shown in FIG. 9) of pair-wise correlations of fMRI time-series sampled on the ECoG electrodes shown in FIG. 6A. FIG. 7A depicts a plot 700 of an estimate of RSN identity of each surface locus in an individual based on supervised classification of seed-based BOLD correlation maps. FIG. 7B depicts a diagram 710 of exemplar BOLD time-series after sampling surface-processed time-series to electrodes using the weighting function described in FIGS. 6A-6G. FIG. 7C depicts a temporal correlation matrix 720 of BOLD signal between all pairs of electrodes after spline regression of distance-related correlation trends (see FIG. 8C). FIG. 7D depicts a plot 730 of rfMRI correlation with electrode index. FIG. 7E depicts a plot 740 of residual rfMRI correlation with distance. FIG. 7F depicts another plot 750 of rfMRI correlation with electrode index.

FIGS. 8A-8F illustrate ECoG preprocessing that may be performed by computing device 904 (shown in FIG. 9). FIG. 8A depicts a plot 800 of 10 Hz signals filtered from two exemplar channels. Thin lines indicate the filtered LFP (carrier wave). Thick lines indicate the band-limited power envelope. FIG. 8B depicts a plot 810 of Euclidean distance across all pairs of electrodes. FIG. 8C depicts a plot 820 of a relationship of correlation values to electrode distance in raw data with a two parameter fit. FIG. 8D depicts a plot 830 of pairwise temporal correlation between electrodes corresponding to the data in plot 820. FIGS. 8E and 8F depict plots 840 and 850, respectively, of correlations after re-referencing data to a common average.

Discussion

The example experiments indicate that there is a frequency specificity to intrinsic and extrinsic resting state networks. More specifically, the experiments indicate that intrinsic networks are associated with theta rhythms, while extrinsic networks are associated with intrinsic networks. In the condition of depression, there is evidence that the intrinsic network appears to dominate over the extrinsic network.

In one embodiment of the present disclosure, an EEG headset is used to provide a non-invasive evaluation of the relationship between intrinsic and extrinsic network interactions. Specifically, the EEG headset provides a measure between the theta and alpha rhythm activity from specific areas on the head associated with the intrinsic and extrinsic networks. For intrinsic network activity, in at least some embodiments, the EEG headset is positioned in a location corresponding to the lateral temporal lobe in EEG locations (T3 on the 10-20 EEG system). For extrinsic activity, in at least some embodiments, the EEG headset is positioned in a location corresponding to the posterior lateral frontal lobe (C3 or CZ on the 10-20 EEG system).

The relationship of theta/alpha activity, or the "Depression Index," may then be visualized relative to a baseline. Specifically, a baseline activity is acquired using the EEG headset and ongoing data is taken to assess the changes in this relationship. Measuring this relationship over several different time scales may be useful for distinct clinical applications. For example, a slow time scale (e.g., days to months) may be useful as an objective measure of impact depression therapy. The Depression Index may be used before and after a mood intervention (e.g., antidepressant medication) to provide a quantitative assessment of impact of therapy. This objective measurement using the Depression Index may be an improved option for therapy over current standards of self-assessment, which are subjective. A fast time scale (e.g., seconds) may be useful to provide real time visualization of the Depression index using the EEG headset, which would allow the user of the headset to alter their balance between brain activity associated with the intrinsic and extrinsic system. In changing this balance, this could fundamentally alter the person's mood. This may provide a novel therapy for depression by altering the pathologic balance of intrinsic and extrinsic network activity.

In one embodiment, the EEG headset includes a simple headset coupled to a computing device (e.g., a mobile phone) providing signal recording, visualization, and feedback. Software associated with the EEG headset may be available for download to the computing device (e.g., as an "app"). In some embodiments, the software may include "gamified" functions and capabilities, to gamify a user's alteration of their network interactions.

Frequency Specificity of fMRI RSNs

The above-described results concern the spectral dependence of the spatial correspondence between fMRI and electrophysiologic correlation patterns. High ECoG:fMRI correspondence was observed for high-gamma BLP (60-100 Hz) and low frequency BLP (<25 Hz, maximal within the 4-13 Hz range) and a minimum of correspondence was observed for low-gamma frequency BLP (25-50 Hz). These findings are extended by revealing previously un-described correspondence at lower BLP frequencies (4-25 Hz). Thus, these results demonstrate that ECoG:fMRI correspondence occurs in two distinct spectral regimes in resting state brain activity. These regimes recall the association of gamma synchronization together with low-frequency desynchronization, which features are ubiquitously observed in ECoG responses to a wide variety of task paradigms. While these task-induced responses are opposite in sign, spatial correspondence spectra (FIGS. 1A-3D) are positive for both frequency regimes. This apparent discrepancy can be reconciled by considering that simultaneous increases or decreases of spontaneous BLP power within RSNs are both expected to produce positive temporal correlations which, in turn, produce ECoG:fMRI spatial correspondence.

Intrinsic Electrophysiological Activity Differentiates the Intrinsic vs. Extrinsic Systems Importantly, regional specificity was observed in the low frequency regime. Specifically, correspondence in the alpha (8-12 Hz) and theta (4-8 Hz) bands was found within the extrinsic and intrinsic functional systems, respectively. These spectral associations are present in both task-based, non-invasive EEG and invasive ECoG measurement methods, as well as spontaneous activity. The above-described results show that these spectral features, which have been previously associated with specific cognitive domains, are topographically linked to RSNs known to instantiate extrinsic vs. intrinsic functionality. Task engagement of the intrinsic system enhances theta oscillations whereas engagement of the extrinsic systems suppresses alpha oscillations. However, either effect, occurring synchronously within a distributed functional system, may generate BLP temporal correlations consistent with the present results. Thus, these findings link the topographies of the extrinsic vs. intrinsic functional systems (and by extension, their associated cognitive domains) with spatially segregated alpha (8-12 Hz) vs. theta (4-8 Hz) intrinsic oscillatory activity.

These results are consistent with the phylogenetically ancient, anatomical dichotomy between the cortico-hippocampal vs. the thalamo-cortical systems. Theta rhythms are organized in the hippocampus, a structure associated with the default mode network, a core component of the intrinsic system. Moreover, the hippocampus is anatomically connected primarily with prefrontal and parietal higher-order association cortices, as opposed to primary sensory-motor areas. In contradistinction, alpha rhythms are generated by thalamo-cortical circuits and are most clearly recorded over primary sensory-motor areas, structures associated with extrinsic functions. Thus, the present results add an electrophysiologic dimension to the dichotomy between the intrinsic vs. extrinsic functional systems defined by R-fMRI.

Relation to BOLD fMRI Frequencies

For BLP envelopes derived from both low (theta/alpha) and high (gamma) frequency carrier waves, peak ECoG: fMRI correspondence was observed at envelope modulation frequencies centered slightly above 0.1 Hz (plots 400 and 425 in FIGS. 4A and 4B, respectively). This peak extended broadly from 0.01 Hz to 1 Hz for both theta/alpha and gamma BLP correlations. This modulation frequency range is consistent with gamma BLP, but is above the range of coherent BOLD fMRI fluctuations responsible for resting-state network correlations, which extends up to but not beyond 0.1 Hz. The apparent spectral discrepancy between ECoG BLP envelope frequencies and BOLD coherence probably represents the low-pass filter characteristics of the BOLD hemodynamic response function acting on electrophysiology that extends to slightly higher frequencies.

Cross-Frequency Coupling

Phase-amplitude coupling (PAC), i.e., amplitude modulation of fast electrophysiological activity by the phase of slower activity, is increasingly recognized as a fundamental organizing principle of the brain's electrical activity. PAC classically refers to the modulation of gamma amplitude by the phase of theta or alpha frequency oscillations, which is thought to control the tight modulation of excitability on the timescale of stimuli and behavioral responses. The present results indicate that infra-slow fluctuations of intrinsic electrophysiological rhythms in the paired theta/gamma as well as alpha/gamma frequency ranges are specific to the intrinsic and extrinsic functional systems, respectively. These findings coincide with the spatio-spectral organization of PAC in spontaneous activity: Foster and colleagues reported that theta-gamma coupling was strongest within the posterior precuneus cortex (PCC) whereas alpha-gamma coupling was strongest within primary visual cortex. The PCC is a core component of the DMN, an intrinsic system network, whereas visual cortex is a component of the extrinsic system.

PAC and the presently reported infra-slow amplitude envelope correlations represent manifestations of spatio-spectral specificity at two different time-scales. PAC concerns gamma power modulations on a timescale of 100-200 ms, whereas our results concern the modulation of the amplitude of both low and high frequency oscillations on the much longer (5-10 s) infra-slow timescale. However, infra-slow activity may modulate gamma activity as a result of recursive hierarchical nesting, whereby infra-slow activity modulates theta/alpha waves which, in turn, modulate gamma activity. Indeed, the spatio-spectrally specific PAC reported by Foster and colleagues was itself modulated by a infra-slow (~0.8 Hz) fluctuation.

Methodological Considerations

The methods and results described herein incorporate several methodological innovations in the comparison of ECoG and fMRI data that may account for enhanced detection of spectral differences between systems. Single subject resting state fMRI is technically challenging because of the limited signal to noise ratio and high prevalence of head motion. These challenges were addressed by extended fMRI data acquisition times (average 60 minutes), exclusion of fMRI volumes contaminated by head motion from computation of correlations, and additional removal of structured noise using ICA. Anatomical registration of fMRI data included compensation for echo planar imaging-related distortions. To improve registration of fMRI data with electrodes, knowledge of the local cortical surface geometry was incorporated in weighting the contribution of the fMRI signal at each electrode. Electronic fMRI noise was reduced by geodesic smoothing on the cortical surface. These maneuvers, in combination, reduced cross-gyral contamination and improved spatial specificity while preserving the fMRI signal to noise ratio.

Correlations of both electrophysiologic and fMRI signals are systematically greater at short distances (see FIGS. 7A-7F and FIGS. 8A-8F). A systematic relation between correlation and distance is present in fMRI data as well as ECoG at BLP frequencies. This relation necessarily increases the spatial similarity of ECoG and BOLD correlation maps because local correlations dominate the fine spectral differences in ECoG:BOLD correspondence if not removed. Previous attempts to control for this effect have excluded nearby electrodes or removed the relation between correlation and distance with a linear model. However, because correlation is inversely proportional to distance (see FIGS. 7A-7F and 8A-8F), modeling this effect as linear in distance induces artifactual long distance correlations, which may generate spurious similarity between ECoG and BOLD correlation maps. Therefore, to increase sensitivity to RSN topography, the correlation:distance relationship was removed by computing device 904 (shown in FIG. 9) using nonlinear (B-spline) regression.

Conclusion

The results show that the temporal frequencies previously associated with task-induced responses are specifically present in the correlation structure of spontaneous electrophysiological activity within the intrinsic and extrinsic functional systems. The present disclosure suggests that this observation extends to the temporal frequency domain. Thus, based on the available evidence, it is proposed that spontaneously activity constrains both the spatial topography and spectral organization of task-induced responses.

Experimental Procedures

Image Acquisition and Preprocessing

Structural and functional imaging was performed for six subjects (see Table 1 for subject profiles) with a 3T Tim Trio Scanner (Siemens, Erlangen, Germany) using product sequences. Functional images were acquired using a BOLD contrast sensitive gradient echo echo-planar sequence (parameters) during which participants were instructed to fixate on a visual cross-hair, remain still and not fall asleep. Anatomical imaging included one sagittal T1-weighted magnetization prepared rapid gradient echo (MP-RAGE) scan (T1W) and one T2-weighted scan (T2W).

fMRI preprocessing proceeded was performed with image distortion correction using the FUGUE module in FSL and field maps were approximated. Distortion correction and motion correction were combined in one resampling step to generate volumetric time-series in Talairach atlas space (3×3×3 mm$^3$ cubic voxels).

Additional preprocessing in preparation for FC analyses included motion censoring based on the DVARS (temporal derivative of RMS BOLD signal across voxels) measure. Motion censoring was computed before de-noising to avoid FC analyses of frames (volumes) with "cosmetically" improved DVARS values but retained artifact. The DVARS censoring threshold was set at 0.5% root-mean-square frame-to-frame BOLD signal change following 20 mm spatial pre-blur in each direction. Epochs containing fewer than 10 contiguous frames meeting the DVARS criterion were excluded from the functional connectivity computations. The fraction of censored data from each participant is listed in Table 1.

Following motion censoring, the retained frames were made zero-mean within each voxel but the data were not otherwise temporally or spatially filtered. Initial de-noising was accomplished using a strategy similar to CompCor. Nuisance regressors were derived from white matter and ventricle masks, segmented in each individual using Free-Surfer, then spatially resampled in register with the functional data. Nuisance regressors also were extracted from voxels in the extra-axial CSF space exhibiting high (greater than 2.5%) temporal standard deviation. Nuisance regressors also were derived from rigid body head motion correction. Following nuisance regression, the volumetric time-series were further de-noised using an ICA regression approach. Because of the small number of subjects (n=6) in this study, components for all subjects were manually classified according to known criteria. Unambiguously artifactual components were eliminated by linear regression. The global signal averaged over the whole brain and its temporal derivative was removed by linear regression. fMRI time-series were prepared for comparison to ECoG data by ribbon-constrained volume to surface resampling using the Human Connectome Project pipeline.

Resting state network topographies were computed in each subject using a supervised classification method. This technique employs a neural network (specifically, a multi-layer perceptron performing non-linear regression) that has been trained to associate correlation maps of a standard set of task-derived seed regions with pre-defined RSN labels. Seed-based fMRI correlation maps generated at every brain locus were classified to produce RSN topographies throughout the brain.

Electrode Registration

After electrode implantation (FIG. 6A), a post-operative CT image (FIG. 6B) was registered (6-parameter rigid body) to the pre-operative T1 image (FIG. 6C). Post-implantation, ECoG electrodes generally are displaced downwards relative to the pre-operative brain surface owing to traction generated by dural over-sewing. To correct this displacement, electrodes were projected to a highly smoothed pial surface (a modified FreeSurfer segmentation) using normal vectors computed from grid and strip geometry (FIG. 6D). Following this correction, total electrode localization error was estimated as ~2 mm.

Imaging-Based Electrode Exclusion fMRI data characteristically are compromised by focal areas of signal dropout caused by magnetization susceptibility inhomogeneities. To accommodate this problem, an intensity iso-surface was computed at 50% of the mean brain value. Electrodes more than 5 mm distant from the iso-surface were excluded from the ECoG:fMRI analyses. See Table 1, Rejected (Imaging) column.

Sampling BOLD Data to Electrodes

After registration of electrode coordinates to individual cortical surfaces (FIG. 6E), surface fMRI time-series were projected to each electrode according to the expected relative contribution of each brain locus modeled under electrostatic assumptions. Specifically, the cerebral grey matter was modeled as a sheet of diploes oriented normal to the cortical mid-thickness surface. The angular component of the dipole was ignored because it was empirically determined that small errors in electrode registration relative to the cortical ribbon geometry led to numerical instability. Thus, the forward solution was modeled by the inverse square of the distance from cortical mid-thickness surface vertices ($r_j$) to points on the electrode surface ($r_i$). The contribution to electrode e of cortical surface vertices j were found by integrating over all elements i of the electrode surface $S_e$:

$$w_{ej} = \int_{i \in S_e} \|r_i - r_j\|^{-2} dS_e$$

The surface map of weights for electrode e, $w_{e\cdot}$, was normalized to unit sum:

$$\overline{w}_{ej} = \frac{w_{ej}}{\sum_{j \in S} w_{ej}}$$

These weights were expressed as a matrix, W, of dimension [electrodes×cortical vertices]. W was used to sample cortical surface maps of each frame of the fMRI time-series, $f(t)$, onto the space of electrodes: $f_e(t)=Wf(t)$. $f_e(t)$ was subsequently used to compute the fMRI temporal correlation matrix in electrode space, thereby ensuring that the fMRI and ECoG data were analyzed identically. The same sampling weights were used for sampling RSN network membership estimates to electrodes for classifying electrodes into RSNs. The weight matrix W was also used for illustrative purposes to create surface displays of correlation maps computed in electrode space, e.g., the topographies in FIGS. 1A-1F.

ECoG Data Acquisition and Preprocessing

Implanted electrodes (platinum, 4 mm, 2.3 mm exposed, PMT corporation) were 8×8 or 6×8 grids (with 1 cm spacing) and strips (1×4, 1×6, or 1×8), placed subdurally facing the cortical surface. A separate strip facing the skull served as ground and reference for the amplifier (Proamp, Lamont Medical Inc). Data were screened for channels with excessive noise and epochs with excessive environmental noise across all channels. Channels exhibiting inter-ictal activity also were excluded.

ECoG signals were referenced to a common average. A de-spiking function, $f(x)=A*a\tan(x/A)$, where A is 5 s.d. of the signal, was applied to attenuate transient artifacts from medical devices (e.g., IV pumps). Data were further inspected for artifact in the time-frequency domain. Ictal events were identified by clinical staff. Sleep epochs were defined behaviorally with video records. Additionally, periods of sustained delta power (>20% power in the 0.5-4 Hz range) were identified as slow wave sleep (SWS) and excluded. The present ECoG:fMRI analyses include only ECoG recordings at least 30 minutes separated from behaviorally identified sleep (from video recordings) or electrophysiologically identified SWS. ECoG data recorded up to 2 hours following ictal events also were excluded.

ECoG signals were decomposed into frequency components by zero-phase digital filtering using a 2nd order Butterworth filter in the forward and reverse directions (effectively, 4th order). Frequency bin edges were logarithmically spaced with cut-off frequencies at $2^k$, where k ranges from 0 to 7 in increments of 0.1. Filtered signals were squared to produce instantaneous power, then further band-pass filtered to isolate specific envelope frequency components. For a given carrier frequency, envelopes were filtered with logarithmically spaced bins with edges defined by $2^k$, where k ranges from −2.5 to 1.25 in increments of 0.25. For each carrier frequency, the upper limit for envelope frequencies to be analyzed was defined as by the bin width used to filter the carrier.

BOLD-ECoG Comparison Methodology

Correlation maps were computed as the Pearson product-moment correlation across all pairs of electrode time-series, treating the fMRI and ECoG BLP time-series identically. Correlations of both ECoG and BOLD signals are systematically greater at shorter distances. Locally increased correlations may be induced by spatial smoothing of BOLD data or volume conduction of deep source in ECoG data. However, distant dependent correlations are expected to be largely driven by true physiologic correlation. Such systematic correlation:distance relationships increase the apparent similarity of ECoG and BOLD correlation maps and therefore decrease the sensitivity of ECoG:fMRI spatial correlations to topographically specific features. The inverse relation of correlation to distance can artifactually introduce long-distance correlations if the distance dependence is removed by linear regression. Thus linear distance regression can generate spurious similarity between ECoG and BOLD correlation maps. Therefore, to maximize sensitivity to RSN topography, the correlation:distance relationship was removed using B-spline regression (see FIGS. 7A-7F and 8A-8F).

After removal of the correlation:distance relationship using B-spline regression, ECoG:fMRI correspondence was computed as the Fisher z-transformed spatial correlation of the ECoG band-limited power (BLP) and fMRI correlation maps. This procedure was computed parametric in carrier and envelope frequency, thereby producing carrier frequency×envelope frequency correspondence spectra for each electrode (e.g., plot 120 in FIG. 1C). As a final step, correspondence spectra were smoothed with a moving average filter (span of 5 bins) in log frequency space.

TABLE 1

Patient characteristics and experimenta data.

| | | | BOLD Data | | ECoG Data | | | | |
| | | | r-fMRI | | ECoG | | | Electrode Inclusion | |
| Participants | | | Data | Frames | Data | | | Rejected | Rejected |
| Patient | Sex | Age | (mins) | Rejected | (mins) | Epochs | Total | (Imaging) | (Ephys) |
|---|---|---|---|---|---|---|---|---|---|
| PT1 | F | 14 | 66.0 | 5.9% | 135.6 | 5 | 100 | 24 | 0 |
| PT2 | M | 15 | 73-3 | 4.9% | 387.6 | 19 | 116 | 18 | 4 |
| PT3 | M | 19 | 58.7 | 3.6% | 703.1 | 15 | 88 | 2 | 0 |
| PT4 | M | 19 | 44.0 | 3.3% | 194.0 | 5 | 64 | 0 | 3 |
| PT5 | M | 55 | 54.9 | 5.2% | 293.0 | 6 | 84 | 7 | 2 |
| PT6 | F | 12 | 62.2 | 14.3% | 241.0 | 10 | 70 | 12 | 3 |
| Average: | | 22 | 60 | 6.2% | 326 | 10 | 87 | 11 | 2 |

EQUIVALENTS AND SCOPE

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. It is also noted that the terms "comprising", "including", "having" or "containing" are intended to be open and permits the inclusion of additional elements or steps.

What is claimed is:

1. A brain computer interface (BCI) system comprising:
at least one electroencephalogram (EEG) electrode; and
a computing device communicatively coupled to the at least one EEG electrode, the computing device comprising a memory, a processor and a display device, the memory storing instructions that, when executed by the processor, cause the processor to:
measure, using the at least one EEG electrode, a first signal from a patient;
band-pass filter alpha band frequencies corresponding to baseline extrinsic network activity and theta band frequencies corresponding to baseline intrinsic network activity from spectral content of the first signal;
generate, based on the baseline extrinsic and intrinsic network activity, a baseline depression index and store the baseline depression index in the memory;
measure, using the at least one EEG electrode, a second signal from the patient;
band-pass filter alpha band frequencies corresponding to current extrinsic network activity and theta band frequencies corresponding to current intrinsic network activity from spectral content of the second signal;

generate a current depression index based on a relationship between the current extrinsic network activity and the current intrinsic network activity;

display, on the display device, a representation of a relationship between the current depression index and the stored baseline depression index; and display, on the display device, an interactive environment, the interactive environment being responsive to at least one of the current depression index and the current extrinsic and intrinsic network activity.

2. The BCI system of claim 1, wherein the computing device comprises a mobile device.

3. The BCI system of claim 2, wherein the computing device comprises a mobile phone.

4. The BCI system of claim 1, wherein a first electrode of the at least one EEG electrode is positioned to monitor a lateral temporal lobe location of the patient.

5. The BCI system of claim 4, wherein the lateral temporal lobe position is T3 on a 10-20 EEG system.

6. The BCI system of claim 4, wherein a second electrode of the at least one EEG electrode is positioned to monitor a posterior lateral frontal lobe location of the patient.

7. The BCI system of claim 6, wherein the posterior lateral frontal lobe location is one of C3 and CZ on a 10-20 EEG system.

8. The BCI system of claim 1, wherein the at least one EEG electrode comprises an invasive EEG electrode.

9. A method of using a BCI system including at least one electroencephalogram (EEG) electrode, a display device, and a computing device communicatively coupled to the at least one EEG electrode and the display device, the method comprising:

measuring, using the at least one EEG electrode, a first signal from a patient;

band-pass filtering alpha band frequencies corresponding to baseline extrinsic network activity and theta band frequencies corresponding to baseline intrinsic network activity from spectral content of the first signal;

generating a baseline depression index based on a relationship between the baseline extrinsic network activity and the baseline intrinsic network activity, and storing the baseline depression index in a memory;

measuring, using the at least one EEG electrode, a second signal from the patient;

band-pass filtering alpha band frequencies corresponding to current extrinsic network activity and theta band frequencies corresponding to current intrinsic network activity from spectral content of the second signal;

generating, by the computing device, a current depression index based on a relationship between the current extrinsic network activity and the current intrinsic network activity;

displaying, on the display device, a representation of a relationship between the current depression index and the stored baseline depression index; and displaying, on the display device, an interactive environment, the interactive environment being responsive to at least one of the current depression index and the current extrinsic and intrinsic network activity.

10. The method of claim 9, wherein band-pass filtering baseline extrinsic network activity and the baseline intrinsic network activity of the patient and generating the baseline depression index are performed before a mood intervention is attempted for the patient.

11. The method of claim 10, wherein band-pass filtering the current extrinsic network activity and the current intrinsic network activity and generating the current depression index are performed after the mood intervention is attempted for the patient.

12. The method of claim 9, wherein measuring the second signal and band-pass filtering alpha band frequencies corresponding to the current extrinsic network activity of the patient comprises monitoring a lateral temporal lobe location using the at least one EEG electrode.

13. The method of claim 12, wherein measuring the second signal and band-pass filtering theta band frequencies corresponding to the current intrinsic network activity of the patient comprises monitoring a posterior lateral frontal lobe location using the at least one EEG electrode.

14. A mobile communications device comprising:
a headset removably attached to the mobile communications device, the headset comprising:
at least one speaker to output audio from the mobile communications device;
a band configured to be positioned adjacent a head of a patient;
at least one electrode coupled to the band;
a processor,
a display device, and
a memory, the memory storing instructions that, when executed by the processor, cause the processor to:
measure, using the at least one electrode, a first signal from the patient;
band-pass filter alpha band frequencies corresponding to baseline extrinsic network activity and theta band frequencies corresponding to baseline intrinsic network activity from spectral content of the first signal;
generate a baseline depression index based on a relationship between the baseline extrinsic network activity and the baseline intrinsic network activity, and store the baseline depression index in the memory;
measure, using the at least one electrode, a second signal from the patient;
band-pass filter alpha band frequencies corresponding to current extrinsic network activity and theta band frequencies corresponding to current intrinsic network activity from spectral content of the second signal;
generate a current depression index based on a relationship between the current extrinsic network activity and the current intrinsic network activity;
display, on the display device, a representation of a relationship between the current depression index and the stored baseline depression index; and
display, on the display device, an interactive environment, the interactive environment being responsive to at least one of the current depression index and the current extrinsic and intrinsic network activity.

15. A brain computer interface (BCI) system comprising:
at least one non-invasive or invasive electroencephalogram (EEG) electrode; and
a computing device communicatively coupled to the at least one non-invasive or invasive EEG electrode, the computing device comprising a memory, a processor and a display device, the memory storing instructions that, when executed by the processor, cause the processor to:
measure, using the at least one non-invasive or invasive EEG electrode, a first signal from a patient;

generate a baseline depression index based on alpha band and theta band spectral content from the first signal, and store the baseline depression index in the memory;

measure, using the at least one non-invasive or invasive EEG electrode, a second signal from the patient;

generate a current depression index based on alpha band and theta band spectral content from the second signal;

display, on the display device, a representation of a relationship between the current depression index and the stored baseline depression index; and display, on the display device, an interactive environment, the interactive environment being responsive to at least one of the current depression index and alpha band and theta band spectral content from the second signal.

* * * * *